(12) United States Patent
Merzougui et al.

(10) Patent No.: US 9,257,705 B2
(45) Date of Patent: Feb. 9, 2016

(54) METHOD FOR PRODUCING PT-FREE ELECTROCATALYSTS FOR FUEL CELLS AND BATTERIES

(71) Applicants: King Fahd University of Petroleum and Minerals, Dhahran (SA); King Abdulaziz City for Science and Technology, Riyadh (SA)

(72) Inventors: Belabbes Ahmed Merzougui, Dhahran (SA); Saheed Abidemi Bukola, Dhahran (SA); Adeola Akeem Akinpelu, Dhahran (SA); Zain Hassan Abdallah Yamani, Dhahran (SA); Tahar Laoui, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 151 days.

(21) Appl. No.: 14/224,163

(22) Filed: Mar. 25, 2014

(65) Prior Publication Data

US 2015/0280245 A1 Oct. 1, 2015

(51) Int. Cl.
| | |
|---|---|
| *H01M 4/02* | (2006.01) |
| *H01M 4/90* | (2006.01) |
| *H01M 4/88* | (2006.01) |
| *H01M 12/08* | (2006.01) |
| *H01M 12/04* | (2006.01) |
| *G01N 27/30* | (2006.01) |

(52) U.S. Cl.
CPC ........... *H01M 4/9016* (2013.01); *G01N 27/308* (2013.01); *H01M 4/885* (2013.01); *H01M 4/8882* (2013.01); *H01M 4/9083* (2013.01); *H01M 12/04* (2013.01); *H01M 12/08* (2013.01)

(58) Field of Classification Search
CPC .... G01N 27/308; H01M 12/04; H01M 12/08; H01M 4/885; H01M 4/8882; H01M 4/9016; H01M 4/9083
See application file for complete search history.

(56) References Cited

U.S. PATENT DOCUMENTS

| | | | | |
|---|---|---|---|---|
| 2009/0208780 | A1* | 8/2009 | Sun | B82Y 30/00 429/528 |
| 2012/0088187 | A1* | 4/2012 | Wu | B01J 31/1815 429/527 |

FOREIGN PATENT DOCUMENTS

| | | | |
|---|---|---|---|
| CN | 103041827 A | 4/2013 | |
| JP | 61-281128 A | * 12/1986 | ............. C08G 73/00 |

OTHER PUBLICATIONS

M. Baibarac, et al., "Covalent functionalization of singled-walled carbon nanotubes by aniline electrochemical polymerization", Carbon, vol. 42, Issue 15, 2004, (1 page).

Yan-Sheng Zhang, et al., "Oxidation-Reduction Reaction Driven Approach for Hyrdothermal Synthesis of Polyaniline Hollow Spheres with Controllable Size and Shell Thickness", The Journal of Physical Chemistry C, 2009, (2 pages).

* cited by examiner

*Primary Examiner* — Patrick Ryan
*Assistant Examiner* — Ben Lewis
(74) *Attorney, Agent, or Firm* — Oblon, McClelland, Maier & Neustadt, L.L.P.

(57) ABSTRACT

A method for synthesizing a nitrogen-doped carbon electrocatalyst by performing selective catalytic oxidative polymerization of solid aniline salt on a carbon support with a catalytic system containing $Fe^{3+}/H_2O_2$ to obtain a mixture, and then heat treating the mixture under a nitrogen atmosphere at 900° C.

16 Claims, 4 Drawing Sheets

FIG. 2A
FIG. 2B
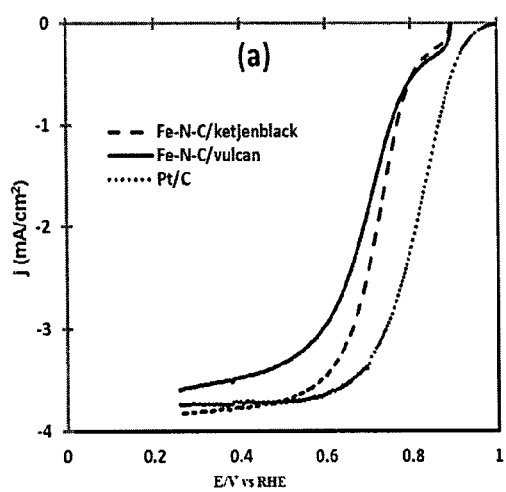
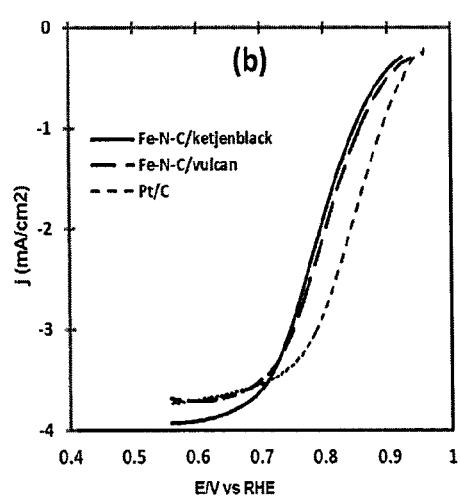

METHOD FOR PRODUCING PT-FREE ELECTROCATALYSTS FOR FUEL CELLS AND BATTERIES

BACKGROUND OF THE INVENTION

1. Field of the Disclosure

The present invention relates to a nitrogen-doped carbon electrocatalyst, a fuel cell and a metal-air battery containing the electrocatalyst, and a method for making the electrocatalyst.

2. Description of Related Art

In recent years, the development of nitrogen-doped carbon electrocatalysts has gained attention of researchers in the fuel cell and air battery fields owing to the problems relating to the use of Pt-based materials. The slow kinetics of oxygen reduction reaction (ORR), high cost, and low stability of Pt-catalysts had been the most important factors impeding the mass commercialization of fuel cells (Adina M., Pascale J, Bruno J, and Serge P., Phys. Chem. Chem. Phys., 2011, 13, 21600-21607; R. Bashyam and P. Zelenay, Nature, 2006, 442, 63-66—each incorporated by reference in its entirety). Nitrogen-doped carbon, however, had been recognized as a potential Pt-free catalyst for fuel cells (Hali P, Changting H, Jinhua C, Bo L, Yafei K, Xiaohua Z, (2010) J. Solid State Electrochem 14:169; Liang H C, chen F, Li R G, Wang L, Deng Z H (2004) Electrochim Acta 49:3463—each incorporated by reference in its entirety).

Investigators have employed ammonium peroxydisulfate $\{(NH4)_2S_2O_8, APS\}$ for the stoichiometric polymerization of aniline (PANI) on a carbon support as a potential fuel cell electrocatalyst. G. Wu et al. (2011) used APS for polymerization of liquid aniline with ketjenblack carbon (KB) and obtained good ORR activity. Also, Lei Fu et al. (2010) developed activated carbon/polyaniline (PANI) with a good ORR activity by using the same APS as a main oxidant for polymerization of liquid aniline. Furthermore, APS oxidant was also employed by B. Merzougui et al. (2013) to deposit PANI from liquid aniline on multi-walled carbon nanotubes.

In an effort to avoid the use of APS as oxidant, Zelenay et al. (2010) of Los Alamos Laboratory came up with a simple synthesis method of sulfur-free approach by employing $FeCl_3$ as an oxidant for polymerizing liquid aniline to obtain a cathode catalyst. APS is known to be a good oxidant, but its side reaction products are sometimes difficult to remove. It has been noticed that formation of sulfur containing compounds, such as FeS which are known to be poison towards oxygen reduction reaction, could occur. Using APS requires several washings of the produced catalyst and sometimes acid treatment, which in most cases requires a second heat treatment, which is a complicated time consuming step.

BRIEF SUMMARY

An object of the invention is a method for synthesizing a nitrogen-doped carbon electrocatalyst.

In an embodiment the method includes selective catalytic oxidative polymerization of solid aniline salt on a carbon support.

In another embodiment the oxidative polymerization is carried out with a catalytic system comprising $Fe^{3+}/H_2O_2$ to obtain a mixture that is heat treated.

In another embodiment the heat treating process is carried out under a nitrogen atmosphere at 900° C.

In one embodiment of the invention, the solid aniline salt is solid aniline hydrochloride.

In another embodiment, the method further comprises, between the oxidation and the heat treating, filtering the mixture, washing, and then seeding with ammonium carbonate as a seedant.

In another embodiment of the invention, the carbon support is selected from Vulcan and Ketjenblack.

In one aspect of the invention, a molar ratio of aniline salt/$Fe^{3+}$/$H_2O_2$ is 0.2/0.02/0.4, respectively.

BRIEF DESCRIPTION OF THE DRAWINGS

FIG. 2A is a graph showing RDE polarization curves obtained for Fe—N—C/Vulcan, Fe—N—C/ketjenblack and Pt/C in $O_2$ saturated 0.1M $HClO_4$.

FIG. 2B is a graph showing RDE polarization curves obtained for Fe—N—C/Vulcan, Fe—N—C/ketjenblack and Pt/C in $O_2$ saturated 0.1M KOH.

DETAILED DESCRIPTION

The present invention includes a synthesis method to obtain high yield of polyaniline on a carbon support by employing solid aniline salt and a $Fe^{3+}/H_2O_2$ coupled catalytic system. The method results in a much better and improved ORR activity and stability as compared to the state-of-art non-noble metal catalysts and those obtained through the use of APS and $FeCl_3$.

The catalytic system $Fe^{3+}/H_2O_2$ employed herein is inexpensive compared to the use of APS and does not produce solid salt as a by-product other than $H_2O$, which does not in any way affect ORR activity and stability of the catalyst. This method of synthesis is more environmentally friendly and leads to catalyst with suitable properties.

The method involves the development of a stable and highly active non-precious metal catalyst for oxygen reduction reaction (ORR) by selective catalytic oxidative polymerization of solid aniline salt using a $Fe^{3+}/H_2O_2$ catalytic system on one or more carbon supports, which is followed by heat treatment under a nitrogen atmosphere at 900° C. Methods of synthesis have been identified as a determining factor in developing non-precious metal (NPM) catalysts with desirable catalytic properties. A lack of these properties is the shortcomings of Pt-based materials.

In the present method, a novel approach was taken in using solid aniline hydrochloride, which does not require additional additive owing to its high solubility in water. This is preferred to liquid aniline from a toxicity and handling points of view. The carbon support is preferably selected from Vulcan and ketjenblack or any other conductive carbon.

To lessen the presence of residual aniline and to obtain the best yield of polyaniline, the stoichiometric molar ratio for aniline/$Fe^{3+}$/$H_2O_2$ respectively ranged from 0.05-0.3/0.01-0.05/0.1-1.0, preferably from 0.1-0.25/0.01-0.04/0.25-0.75, especially preferably about 0.2/0.02/0.4. To prevent aggregation of PANI precipitate that could reduce active sites for ORR during heat treatment and to obtain a porous fine powder, ammonium carbonate was used as seedant, a sacrificed agent.

Figure 1:
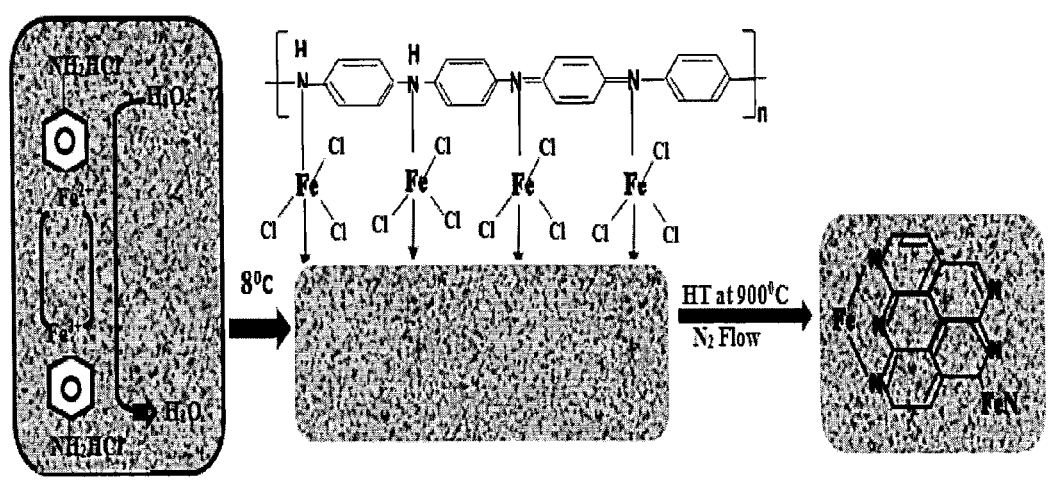
FIG. 1 is a diagram showing a proposed synthesis pathway.
Figure 3A:
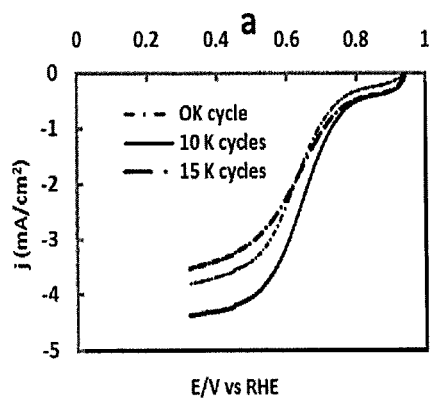
FIG. 3A is a graph showing voltammetry curves before and after cycling in $O_2$ saturated 0.1M $HClO_4$ for Fe—N—C/ketjenblack at 5 mV/s, 900 rpm, and room temperature.
Figure 3B:
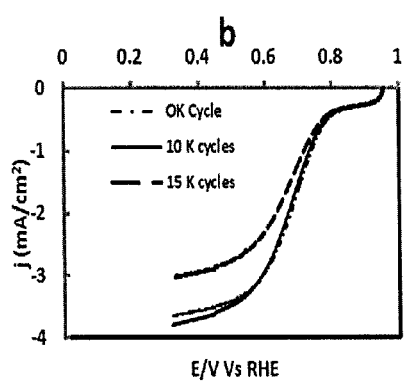
FIG. 3B is a graph showing voltammetry curves before and after cycling in $O_2$ saturated 0.1M $HClO_4$ for Fe—N—C/Vulcan at 5 mV/s, 900 rpm, and room temperature.
Figure 3C:
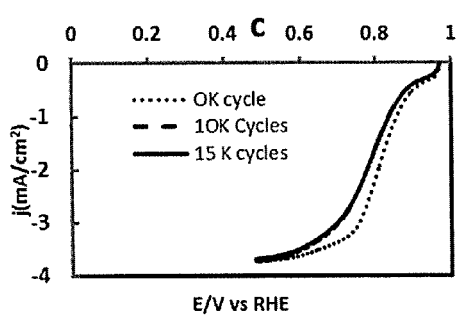
FIG. 3C is a graph showing voltammetry curves before and after cycling in $O_2$ saturated 0.1M KOH for Fe—N—C/ketjenblack at 5 mV/s, 900 rpm, and room temperature.
Figure 3D:
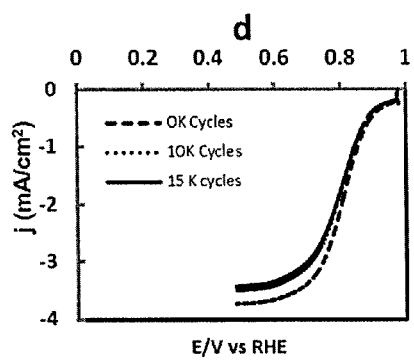
FIG. 3D is a graph showing voltammetry curves before and after cycling in $O_2$ saturated 0.1M $HClO_4$ for Fe—N—C/Vulcan at 5 mV/s, 900 rpm, and room temperature.

Since, oxidative polymerization of aniline is exothermic, temperature influence is an important factor in obtaining high molecular weight of PANI on a carbon support. So, the reaction is carried out at a temperature less than or equal to 10° C., preferably ranging from 6 to 10° C. The proposed synthesis pathway is depicted in FIG. 1.

The synthesis method involves initial pretreatment of the carbon support in an acidic solution at room temperature, preferably 50° C. for a time period ranging from 12 to 20 hours, preferably from 15 to 18 hours. This is necessary to remove any foreign impurities in the carbon supports. The solution medium is selected from the group consisting of hydrochloric acid, acetic acid, boric acid, carbonic acid, citric acid, hydrofluoric acid, nitric acid, and oxalic acid or a mixture thereof. The solution is preferably hydrochloric acid. A concentration of the solution is ranged from 0.25 to 1 M, preferably from 0.5 to 0.75 M. A weight/volume ratio of the carbon support to the acidic solution is from 0.004 g/ml to 0.01 g/ml, preferably from 0.005 g/ml to 0.006 g/ml in order to obtain good dispersion of carbon in the acid solution.

The carbon supports are then filtered, washed with $H_2O$, and vacuum dried at a temperature ranging from 60 to 100° C., preferably from 70 to 90° C., for a time period ranging from 5 to 10 hours, preferably from 6 to 9 hours, especially preferably from 7 to 8 hours. The carbon source is then dispersed in $H_2O$ in a weight/volume ratio ranging from 4 to 10 mg carbon source/1 ml $H_2O$, preferably from 6 to 8 mg carbon source/1 ml $H_2O$. The dispersion is sonicated for 10 to 30 min, preferably 20 min, and then transferred to a water bath maintained at a temperature of from 4 to 12° C., preferably 6 to 10° C., and especially preferably about 8° C., using a circulating bath.

Then, aniline hydrochloride salt is dissolved in $H_2O$ and added to the carbon support. A concentration of the aniline hydrochloride salt in $H_2O$ is from 0.15 to 0.3 M, preferably about 0.2 M. The mixture is kept under stirring for proper impregnation of aniline salt onto the carbon matrix. Thereafter, $FeCl_3.6H_2O$ is dissolved in water and added to the slurry. A concentration of $FeCl_3.6H_2O$ in water is from 0.15 to 0.3M, preferably about 0.2 M.

$H_2O_2$ is added in dropwise to the mixture and the solution mixture is then brought up to a desired volume with $H_2O$. The mixture is left under stirring for 24 hr to ensure complete polymerization of aniline. Upon completion, the mixture is filtered, washed and seeded with ammonium carbonate to prevent aggregation of PANI and to create porosity (later after heat treatment) and thereafter vacuum dried at a temperature ranging from 60 to 100° C., preferably from 70 to 90° C., especially preferably about 80° C. for a time period ranging from 5 to 10 hours, preferably from 6 to 9 hours, especially preferably from 7 to 8 hours. The obtained sample is heat treated in $N_2$ gas at 900° C.

EXAMPLE

The synthesis method involved the initial pretreatment of carbons supports (Vulcan XC-72 and ketjenblack EC300) in 40 ml 0.5M HCl overnight, approximately 15 hr. This is necessary to remove any foreign impurities in the carbon supports. The carbon supports were filtered washed with $H_2O$ and vacuum dried at 70° C. for 7 hr. The reaction volume was set at 100 ml in order to maintain 0.2/0.02/0.4 molar ratio of aniline salt/$Fe^{3+}$/$H_2O_2$ respectively. 0.26 g of the carbon source were dispersed in 40 ml $H_2O$ and sonicated for 20 mins. 0.2M aniline hydrochloride salt (2.592 g, 0.02 mol) was dissolved in 40 ml $H_2O$ then added to the carbon support. The mixture was kept under stirring for proper impregnation of aniline salt onto the carbon matrix. This was transferred to a water bath maintained at 8° C. using a circulating bath. Thereafter, 0.02M $FeCl_3.6H_2O$ (0.512 g, ≈0.002 mol) was dissolved in 10 ml water and added to the slurry. 0.4M $H_2O_2$ (2.68 ml) prepared from 35% $H_2O_2$ was added in dropwise to the mixture and the solution mixture was brought up to 100 ml with $H_2O$. The mixture was left under stirring for 24 hr to ensure complete polymerization of aniline at 8° C. The mixture was filtered, washed and seeded with ammonium carbonate to prevent aggregation of PANI and to create porosity (later after heat treatment) and thereafter vacuum dried at 80° C. for 7 hr. The obtained sample was heat treated in $N_2$ gas at 900° C. (1 hr hold time and 3 hr for ramping temperature from room temperature to 900° C.). The same synthesis condition was repeated for each carbon support. Two different carbon supports, Vulcan and Ketjenblack were used and the obtained catalysts were denoted as Fe—N—C/Vulcan and Fe—N—C/ketjenblack. These catalysts were characterized by using a thin film rotating disk electrode (TF-RDE) for its activity and stability and also by spectroscopy techniques to investigate their morphological structures and composition.

Oxygen Reduction Reaction (ORR) Activity of the Catalysts

The ORR activities of the catalysts were measured using a thin film rotating disk electrode, RDE (Pine Instrument) with a conventional three-electrode electrochemical cell. The working electrode was prepared by depositing 16 μl of the ink suspension on the pre-cleaned glassy carbon substrate (5 mm diameter, Pine Instruments). The catalyst loading used in this work was fixed at 0.6 mg/$cm^2$. A Platinum mesh and Ag—AgCl (calibrated and converted to RHE) were used as counter and reference electrodes respectively. Prior to oxygen reduction reaction measurements, each electrode was potential cycled in nitrogen saturated 0.1M $HClO_4$ or 0.1M KOH for 15-20 cycles between 0 and 1.2 V/RHE at 20 mV/s until a stable Cyclic Voltammogram was obtained. The kinetics of Fe—N—C/Vulcan and Fe—N—C/ketjenblack towards ORR were conducted using linear sweep voltammetry on RDE in oxygen saturated 0.1M $HClO_4$ and 0.1M KOH at 900 rpm with a scan rate of 5 mV/s and compared to that of conventional Pt/C (Pt metal loading, 25 μg/$cm^2$) between 0.65 and 1.0 V/RHE as shown in FIGS. 2A and 2B.

The corresponding onset potentials and half-wave potentials for Fe—N—C/Vulcan and Fe—N—C/ketjenblack were (0.85 V, 0.732 V) and (0.86 V, 0.73 V) respectively in 0.1M HClO$_4$, whereas in 0.1M KOH, the onset and half-wave potentials were (0.95 V, 0.82 V) for Fe—N—C/Vulcan and (0.95 V, 0.802 V) for Fe—N—C/ketjenblack. The half-wave potential was only 78 mV less than that of Pt/C in acidic medium for catalyst Fe—N—C/ketjenblack and 30 mV less than that of Pt/C in alkaline medium. The steady state polarization curves obtained for the two catalysts were analyzed by Koutechy-Levich principle and the results indicate an ORR catalyzed by a four electron transfer process, indicating less formation of hydrogen peroxide intermediates.

Stability of the Catalysts

In a real fuel cell operation condition, cathode catalyst stability still remains a factor hampering fuel cell commercialization for all Pt-based and non-Pt based catalysts. This prompted a prolong durability study on the catalysts obtained through the new synthesis approach. The durability test was investigated by chronoamperommetry experiments in oxygen saturated 0.1M HClO$_4$ and 0.1M KOH between 0.65 and 1.0 V for 15,000 cycles using a square wave signal of 5 s at each potential. This was carried out in a separate electrochemical cell designated for such use. The ORR activities of the cycled catalysts were measured in a fresh electrolyte after every 5,000 cycles (FIGS. 3A, 3B, 3C, and 3D). Unexpectedly, activity gains were observed only in the acidic medium for the first 10,000 cycles. This may be due to full utilization of the catalysts' surface areas due to electrode cycling which is more obvious in Fe—N—C/ketjenblack than Fe—N—C/Vulcan. After 10,000 cycles, the ORR activities tend to stabilize, particularly in alkaline medium. Loss in ORR activity seems to be more significant in the diffusion regime. This may reveal that some change in surface chemistry of catalyst alters diffusion of oxygen through the catalyst layer.

Methanol Tolerance

Figure 4A:
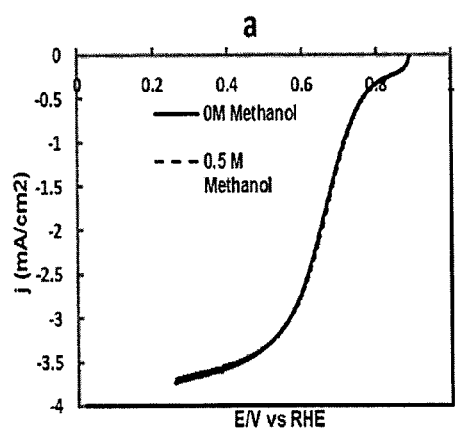
FIG. 4A is a graph showing voltammetry curves in $O_2$ saturated 0.1M $HClO_4$, with and without 0.5M $CH_3OH$ at 5 mV/s, 900 rpm, and room temperature, for Fe—N—C-ketjenblack.
Figure 4B:
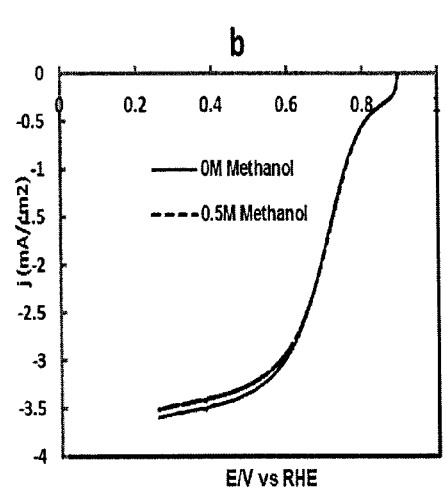
FIG. 4B is a graph showing voltammetry curves in $O_2$ saturated 0.1M $HClO_4$, with and without 0.5M $CH_3OH$ at 5 mV/s, 900 rpm, and room temperature, for Fe—N—C-Vulcan.
Figure 5A:
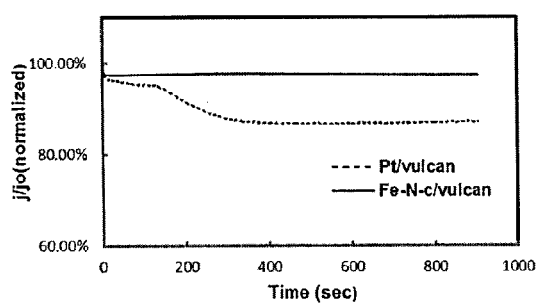
FIG. 5A is a graph showing chronoamperommetry curves (CA) in $O_2$ saturated 0.1M KOH establishing Fe—N—C/Vulcan methanol tolerance as compared to that of Pt/Vulcan at 5 mV/s, 900 rpm, room temperature, 0.5M $CH_3OH$, and 0.8 V potential hold.
Figure 5B:
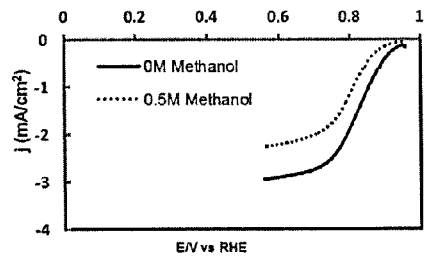
FIG. 5B is a graph showing RDE methanol tolerance for Pt/Vulcan, a significant loss in electrode performance was noticeable when methanol was introduced in the cell.

The catalysts synthesized through this new synthesis method also show remarkable methanol tolerance even at high concentration of 0.5M CH$_3$OH in both acidic and alkaline media (FIGS. 4A and 4B). To further establish their methanol tolerance, chronoamperommetry (CA) test was also conducted at a potential hold 0.8V/RHE for 15 minutes for ORR in only alkaline medium. 0.5M CH$_3$OH was injected into the cell at 180 seconds as indicated by arrows and results were compared to that of Pt/C (FIG. 5A) and (FIG. 5B) for RDE methanol tolerance measurements. A significant drop in activity was observed for Pt/C, whereas Fe—N—C/Vulcan did not undergo any change in electrode performance.

The invention claimed is:

1. A method for synthesizing a nitrogen-doped carbon electrocatalyst, comprising:
    performing selective catalytic oxidative polymerization of a solid aniline salt on a carbon support with a catalytic system comprising Fe$^{3+}$/H$_2$O$_2$ to obtain a mixture;
    filtering the mixture;
    washing the mixture;
    seeding the mixture with ammonium carbonate as a seedant, sacrificed agent; then heat treating the mixture under a nitrogen atmosphere at 900° C.

2. The method of claim 1, further comprising, performing the polymerization at a temperature between 6° C. and 10° C., wherein the temperature is maintained before the polymerization.

3. The method of claim 2, wherein the temperature is about 8° C.

4. The method of claim 1, wherein the carbon support is at least one selected from the group consisting of Vulcan and Ketjenblack or a mixture thereof.

5. The method of claim 1, wherein the carbon support is at least one selected from the group consisting of conducting carbon, vulcan, acetylene black, black pearls, carbon nanotube, graphene, and activated carbon, wherein the carbon support has a surface area between 50 m$^2$/g to 3000 m$^2$/g.

6. The method of claim 1, wherein a molar ratio of aniline salt/Fe$^{3+}$/H$_2$O$_2$ is from 0.05-0.3/0.01-0.05/0.1-1.0.

7. The method of claim 1, wherein a molar ratio of aniline salt/Fe$^{3+}$/H$_2$O$_2$ is from 0.1-0.25/0.01-0.04/0.25-0.75.

8. The method of claim 1, wherein a molar ratio of aniline salt/Fe$^{3+}$/H$_2$O$_2$ is 0.2/0.02/0.4.

9. The method of claim 1, wherein a molar ratio of any nitrogen-containing compound salt/Fe$^{3+}$/H$_2$O$_2$ is 0.2/0.02/0.4.

10. A nitrogen-doped carbon electrocatalyst obtained by the method of claim 1.

11. A fuel cell comprising the nitrogen-doped carbon electrocatalyst of claim 10.

12. A battery comprising the nitrogen-doped carbon electrocatalyst of claim 10.

13. An electrochemical sensor comprising the nitrogen-doped carbon electrocatalyst of claim 10.

14. The method of claim 1, wherein the solid aniline salt is solid aniline hydrochloride.

15. A method for synthesizing a nitrogen-doped carbon electrocatalyst, comprising:
    performing selective catalytic oxidative polymerization of a solid aniline salt on a carbon support with a catalytic system comprising Fe$^{3+}$/H$_2$O$_2$ to obtain a mixture;
    filtering the mixture;
    washing the mixture;
    adding the mixture at least one sacrificed agent selected from the group consisting of ammonium carbonate, ammonium bicarbonate, and sugar; then
    heat treating the mixture under a nitrogen atmosphere at 900° C.

16. A method for synthesizing a nitrogen-doped carbon electrocatalyst, comprising:
    performing selective catalytic oxidative polymerization of a solid aniline salt on a carbon support with a catalytic system comprising Fe$^{3+}$/H$_2$O$_2$ to obtain a mixture;
    filtering the mixture;
    washing the mixture;
    seeding with a sacrificed agent containing only carbon, nitrogen, oxygen, and hydrogen sources;
    heat treating the mixture under a nitrogen atmosphere at 900° C.

* * * * *